Figures 5, 6:
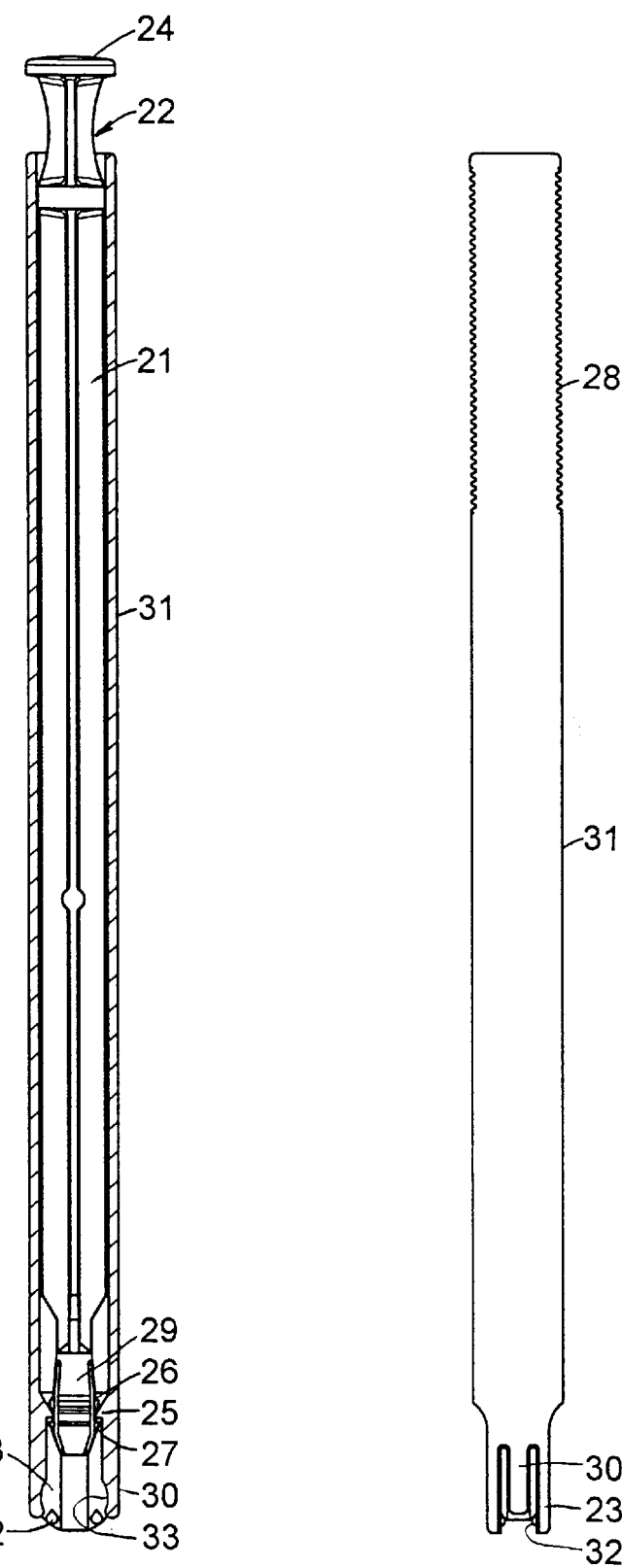

United States Patent [19]
Hofstätter

[11] Patent Number: 5,860,946
[45] Date of Patent: Jan. 19, 1999

[54] INSTRUMENT FOR INSERTING A SUPPOSITORY

[75] Inventor: Thibaud Hofstätter, Helsingør, Denmark

[73] Assignee: Novo Nordisk A/S, Bagsvaerd, Denmark

[21] Appl. No.: 886,588

[22] Filed: Jul. 1, 1997

[30] Foreign Application Priority Data

Jul. 5, 1996 [DK] Denmark .................................. 0752/96

[51] Int. Cl.⁶ ............................................ A61F 13/20
[52] U.S. Cl. ............................ 604/15; 604/57; 604/59; 604/73
[58] Field of Search ................... 604/73, 60–63, 604/57, 59, 11, 15, 27, 28, 49

[56] References Cited

U.S. PATENT DOCUMENTS 3,667,465  6/1972  Voss .
5,681,279  10/1997  Roper et al. ........................ 604/60 X
5,788,664  8/1998  Scalise ................................... 604/15

FOREIGN PATENT DOCUMENTS 2 561 928  10/1985  France .

*Primary Examiner*—John D. Yasko
*Attorney, Agent, or Firm*—Steve T. Zelson; Card E. Rozek

[57] ABSTRACT

In an instrument for inserting a suppository, which instrument comprises a tubular housing (31) with a first end adapted to receive said suppository between two tongues (30) and a second end through which a plunger (22) is inserted in the tube, which plunger has a first end having a circular cross section and two axially spaced circumferential flanges (26, 27) and a second end projecting from the second end of the tube (31). The first end of the tube has an inwardly extending shoulder (25) which engage between said flanges (26, 27) and the first end of the piston is by radial slots divided into an uneven number of sectors (29). The plunger (22) has between its first end and a press button (24) at its second end angular spaced radial walls (21) abutting the inner wall of the tube (31) and axial spaced disc shaped walls are provided having a diameter corresponding to the inner diameter of the tube (31).

5 Claims, 2 Drawing Sheets

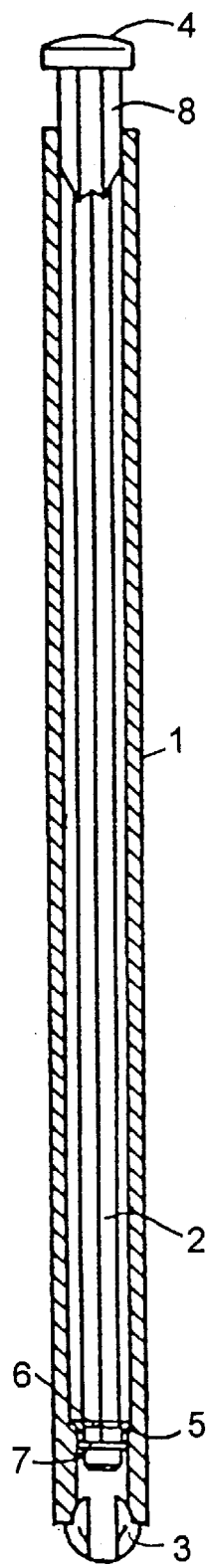
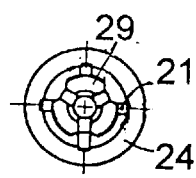
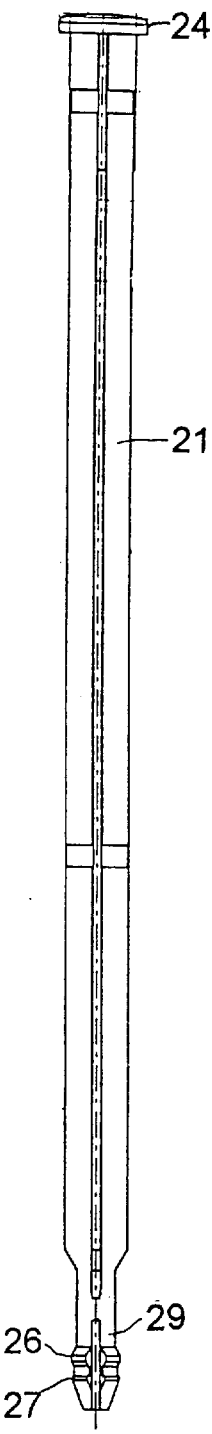
Fig. 1
Fig. 2
Fig. 4
Fig. 3

INSTRUMENT FOR INSERTING A SUPPOSITORY

CROSS-REFERENCE TO RELATED APPLICATIONS

This application claims priority under 35 U.S.C. 119 of Danish application serial no. 0752/96 filed 5 Jul. 1996, the contents of which are fully incorporated herein by reference.

The invention relates to instruments for inserting a suppository, which instruments comprises a tube with a first end adapted to receive said suppository and a second end through which a plunger is inserted in the tube, which plunger has a first end having a circular cross section and two axially spaced circumferential flanges and a second end projecting from the second end of the tube, the first end of the tube having an inwardly extending shoulder which engages between said flanges.

Such an instrument is known from AU 570 785. The suppository is held in the first end of the tube and when the tube has been positioned in vagina the projecting end of the plunger is pressed and the other end of the plunger will then expel the suppository from the tube. Before use the plunger is loosely surrounded by the tube and held in a position with its expelling end immediately behind the suppository stored in the tube. The piston is held in this position by the inwardly extending shoulder at the first end of the tube engaging between the two axially displaced circumferential flanges at the expelling end of the piston. When the instrument is used for positioning the suppository the rear flange is pressed past the inwardly extending shoulder in the tube. The flanges and the shoulder are so dimensioned that a defined pressure is necessary to make the flange pass the shoulder. Hereby an unintentional expelling of the suppository is omitted and at the same time the shoulder engages behind the front flange so that the plunger can not easily be pulled out to give the apparatus its ordinary and unused appearance.

However, the shoulder and the flanges may due to existing tolerances for injection moulded plastic members deviate from an exact circular form and be slightly elliptic. Thereby the pressure it takes to pass the shoulder over the flange may vary depending of whether the axis of the ellipse defining the shoulder corresponds to the axis of the ellipse defining the flange, i.e. whether the piston rod is in such a rotational position that the shoulder pass over the flange with its major axis merging the major axis of said flange or if these two axis are rotated 90° relative to each other. In the first case the resistance against passage of the shoulder over the flange will be lower than intended and in the last case this resistance will be higher.

It is an object of the invention to provide a plunger by which the force which must be exerted on the plunger remains well defined notwithstanding the rotational position of this plunger relative to the shoulder.

This is obtained by the instrument described in the opening of this application, which instrument is according to the invention characterised in, that the first end of the piston by radial slots is divided into a number of sector shaped webs.

Such a plunger does not rely on the resilience of the flanges or the shoulder but on the resilience of the webs which may be bent so far towards each other as allowed by the slots dividing the first end of the plunger into the webs.

In a preferred embodiment of the plunger the number of sectors into which the first end of the plunger is divided is uneven. The uneven number of webs ensures that the force necessary to bend the webs towards each other in a first rotational position of the plunger will not deviate much from the force needed to bend the webs towards each other in a second rotational position perpendicular to the first one.

Whereas the plunger according to the known instrument is a thin rod having a quadratic cross section, the plunger in an appropriate embodiment of the invention may between its first end and a press button formed at its second end comprise angular spaced radial walls abutting the inner wall of the tube. Thereby it is omitted that the plunger bends out in the tube if a heavy pressure is transmitted through the plunger.

In an embodiment according to the invention the plunger may be provided with axial spaced disc shaped walls may be provided having a diameter corresponding to the inner diameter of the tube. By this arrangement the plunger will be further stabilised against out bending.

The suppository may be held in the tube by opposite resilient tongues having in walls facing each other recesses mating an outer contour of the suppository. Thereby the force necessary to expell the tablet will mainly be the same from tablet to tablet.

In the following the invention will be further described with reference to the drawing, wherein FIG. 1 shows a sectional view of an insertion instrument according to the known art, FIG. 2 shows a perspective view of a plunger according to the invention, FIG. 3 shows in an enlarged scale a side view of a plunger according to the invention, FIG. 4 shows in a further enlarged scale an end view of the plunger shown in FIG. 3

FIG. 5 shows a sectional view of a tubular housing with a plunger according to the, and FIG. 6 shows a side view of the housing in FIG. 5.

In FIG. 1 is shown an instrument according to the known art. A plunger 2 having a quadratic cross section is inserted in a tubular housing 1. At an end of the housing 1 lips 3 are provided to support a suppository which may be expelled by the plunger when a button 4 at a projecting end of this plunger is pressed. At its expelling end the plunger 2 has a circular cross section and is provided with axially spaced flanges 6 and 7. An inward shoulder 5 in the tubular housing 1 engages between the flanges 6 and 7 whereby the piston rod is fixed against unintentional axial movement. When the instrument is used it is inserted in vagina, or where the suppository is going to be placed, and the button 4 is pressed. When the pressure is sufficient to overcome the resiliency of the rear flange 6 this flange will be moved past the shoulder 5 and will be locked in this advanced position with the shoulder gripping behind the rear flange 6. The rear end of the plunger has a part 8 with an enlarged cross section to maintain the piston rod running along the axis of the tube.

FIG. 2 shows a plunger 22 according to an embodiment of the invention. This plunger has an expelling end with a mainly circular cross section and provided with axially spaced flanges 26 and 27. Further the part with the circular cross section is divided into three webs 29 which each has a sector shaped cross section. Radial slots between the sectors allow these webs to be bent toward the axis of the plunger.

When the piston rod or plunger is inserted in a housing as shown in FIG. 5 with an inward shoulder 25, this shoulder may engage between the flanges 26 and 27 to maintain the plunger in a first position in the housing. When the button 24 is pressed the rear flange will pass the inward shoulder 25 in the housing by a combined deformation of the resilient flange 26 and a bending of the webs 29 towards each other. As the force necessary to bend the webs 29 towards each other is only little depending on how far the webs are bent, the pressure necessary to move the flange 26 past the inward shoulder 25 will to a minor extent depend on the tolerances of said shoulder 25 and flange 26.

As it is best seen in FIG. 4, the expelling end of the plunger is divided into an odd number of webs. In the shown example this number is three, but five or more webs are possible. An odd number of webs is chosen as an even number will have as a result that at least one of the slots dividing the plunger end into webs runs along a diameter in the circular cross section and the resilience of the webs perpendicular to this diameter would be different from the resilience in any other direction and the passage of the circular shoulder would be dependent on the rotational position of the plunger if the shoulder is not exactly circular.

The body of the plunger 22 is formed by radial walls 21 which have a radial dimension allowing the outer edge of said walls to abut the inner wall of the tubular housing 31 to guide the plunger in this housing and to prevent it from bending out when a pressure is transmitted from the button 24 to the expelling end. Bending out of the plunger will by the user operating the button be felt as a resiliency which will make her feel that it is questionable whether the suppository is dispensed or not.

In the shown embodiment of the insertion instrument the tubular housing 31 has been modified relative to the housing (1) according to the prior art shown in FIG. 1. FIG. 6 shows a side view of the modified housing 31. Recognising that by use of the instrument the button 24 is pressed by the thumb whereas the upper part of the housing 31 is gripped with the two following fingers this upper part is provided with corrugations 28 to avoid that the housing slips between the gripping fingers.

By known art housings as shown in FIG. 1 a tablet to be inserted is held between lips 3 provided with protrusions. The tablet is held by the lips grippingly engaging the slightly arched end walls of the tablet. However, the force of this engagement will vary with the thickness of the tablet and this thickness may actually vary from one tablet to another whereas the diameter of the cylindrical wall of the tablets remains the same.

In an instrument according to the invention a tablet is mainly held between a pair of resilient tongues 30 which have in walls facing each other recesses 33 mating the cylindrical wall of the tablet. Lips 23 with protrusions 32 are provided but are not relied on for securing of the tablet in the instrument but keep the tablet from falling out in its axial direction.

I claim:

1. An instrument for inserting a suppository, which instrument comprises a tube with a first end adapted to receive said suppository and a second end through which a plunger is inserted in the tube, which plunger has a first end having a circular cross section and two axially spaced circumferential flanges and a second end projecting from the second end of the tube, the first end of the tube having an inwardly extending shoulder which engage between said flanges, characterised in that the first end of the piston by radial slots are divided into a number of sectors.

2. An instrument according to claim 1, characterised in that the number of sectors into which the first end of the piston rod is divided is uneven.

3. An instrument according to claim 1, characterised in that the piston between its first end and a press button formed at its second end comprises angular spaced radial walls abutting the inner wall of the tube.

4. An instrument according to claim 3, characterised in that axial spaced disc shaped walls are provided having a diameter corresponding to the inner diameter of the tube.

5. An instrument according to claim 3, characterised in that the suppository is held in the tube by opposite resilient tongues having in walls facing each other recesses mating the outer contour of the suppository.

* * * * *

UNITED STATES PATENT AND TRADEMARK OFFICE
CERTIFICATE OF CORRECTION

PATENT NO.    :    5,860,946

DATED    :    January 19, 1999

INVENTOR(S)    :    Thibaud Hofstätter

It is certified that error appears in the above-identified patent and that said Letters Patent is hereby corrected as shown below:

Col. 4, line 22, delete "engage" and insert --engages--.

Col. 4, line 23, delete "by" and insert --includes--.

Signed and Sealed this

Eighth Day of February, 2000

Attest:

Attesting Officer

Q. TODD DICKINSON

Commissioner of Patents and Trademarks